(12) United States Patent
Tsujii et al.

(10) Patent No.: US 7,676,021 B2
(45) Date of Patent: Mar. 9, 2010

(54) RADIATION IMAGING APPARATUS

(75) Inventors: Osamu Tsujii, Utsunomiya (JP);
Shinsuke Hayashida, Yokohama (JP);
Kazuhiro Matsumoto, Saitama (JP);
Katsushi Kato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 95 days.

(21) Appl. No.: 12/176,093

(22) Filed: Jul. 18, 2008

(65) Prior Publication Data
US 2009/0022269 A1   Jan. 22, 2009

(30) Foreign Application Priority Data
Jul. 20, 2007   (JP) .............................. 2007-189992

(51) Int. Cl.
A61B 6/03 (2006.01)
A61B 6/04 (2006.01)
(52) U.S. Cl. .............................. 378/37; 378/17; 378/20; 378/196; 378/197
(58) Field of Classification Search .................... 378/17, 378/20, 37, 196, 197
See application file for complete search history.

(56) References Cited
U.S. PATENT DOCUMENTS

| 4,926,453 | A | 5/1990 | Toniolo |
| 6,298,114 | B1 * | 10/2001 | Yoda ............................. 378/37 |
| 6,463,122 | B1 * | 10/2002 | Moore ........................... 378/65 |
| 6,480,565 | B1 * | 11/2002 | Ning ............................. 378/37 |
| 6,987,831 | B2 * | 1/2006 | Ning ............................. 378/37 |
| 7,561,661 | B2 * | 7/2009 | Ullberg et al. ................. 378/19 |
| 2004/0052328 | A1 | 3/2004 | Sabol et al. |
| 2005/0074155 | A1 | 4/2005 | Alyassin |
| 2006/0262898 | A1 | 11/2006 | Partain et al. |
| 2007/0121782 | A1 | 5/2007 | Sendai |
| 2007/0133747 | A1 | 6/2007 | Manak et al. |

FOREIGN PATENT DOCUMENTS

| EP | 417964 | | 3/1991 |
| EP | 1864611 | A1 * | 12/2007 |
| FR | 2816822 | | 5/2002 |
| JP | 2003-116825 | | 4/2003 |
| JP | 2004-105729 | | 4/2004 |
| WO | 2006/106927 | | 10/2006 |

* cited by examiner

*Primary Examiner*—Allen C. Ho
(74) *Attorney, Agent, or Firm*—Canon USA Inc IP Div (57) ABSTRACT

A radiation imaging apparatus that performs radiation imaging of a breast of a subject, which includes a table for laying down the subject; a receiving section that receives a breast of the subject laid on the table in a supine position; a radiation imaging section including a radiation emission unit and a radiation detection unit each located at a position opposing to each other being interposed by the breast of the subject received in the receiving section; and a drive unit that shifts the receiving section to a position suitable for imaging the breast of the subject.

10 Claims, 11 Drawing Sheets

BINARY DATA

SCAN FRAME ADJUSTMENT

ADJUSTED TRANSMISSION DATA

FIG. 8A  FIG. 8B  FIG. 8C

TRANSMISSION DATA

PIXEL VALUE HISTOGRAM

FIG. 9A

| CORONAL | CORONAL | CORONAL | CORONAL |

CT IMAGE

BINARY CT IMAGE

SCANNING PLAN

FIG. 9B

| AXIAL | AXIAL | AXIAL | AXIAL |

CT IMAGE

BINARY CT IMAGE

RECONSTRUCTION AREA

SCANNING PLAN

RADIATION IMAGING APPARATUS

BACKGROUND OF THE INVENTION

1. Field of the Invention

The invention relates to a radiation imaging apparatus which takes radiographic images of a breast of a subject.

2. Description of the Related Art

Conventionally, various modifications of mammography apparatus for taking X-ray fluoroscopic images of mammary glands and/or breasts have been proposed.

For example, Japanese Patent Application Laid-Open No. 2003-116825 discusses a technique for obtaining three-dimensional data and calculating volume data in order to increase an amount of diagnostic data.

Also, Japanese Patent Application Laid-Open No. 2004-105729 discusses a technique for obtaining images including three-dimensional data and calculating volume data without pressing a chest region of a subject.

It is well known that the incidence of breast cancer is high in the vicinity of the axillae. This is a reason for adopting medio-lateral oblique (MLO) as an imaging direction in X-ray mammography. It is possible to take images of axillary portions by using an entire body CT scanner, which is capable of taking tomograms of the entire body of a subject. However, the entire body CT scanner has a disadvantage such that portions irrelevant to the diagnosis are exposed to radiation and the reconstruction area is too large, resulting in an unsatisfactory resolution. That is, the chest CT scanner is required to appropriately scan in the vicinity of axilla. However, conventional techniques fail to satisfy the requirement.

When an excision operation is carried out on a cancer portion of a breast while referring to previously taken CT images, the CT images of a subject have to be taken in a posture similar to the posture under operation (i.e., a supine position). However, conventionally there is no X-ray mammography technique capable of capturing an image in a supine position excluding the entire body CT scanner.

SUMMARY OF THE INVENTION

The present invention is directed to a radiation imaging apparatus capable of appropriately scanning a portion adjacent to an axilla.

According to an aspect of the present invention, radiation imaging apparatus adapted to perform radiation imaging of a breast of a subject includes a table for supporting a subject in a supine position, a receiving section configured to receive a breast of the subject whilst in said supine position, a radiation imaging section including a radiation emission unit and a radiation detection unit which face each other and which have the breast of the subject interposed therebetween when the breast is received in the receiving section and a drive unit operable to move the receiving section to a position suitable for imaging the breast of the subject.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will now be described in detail with reference to the drawings.

Figures 1A, 1C:
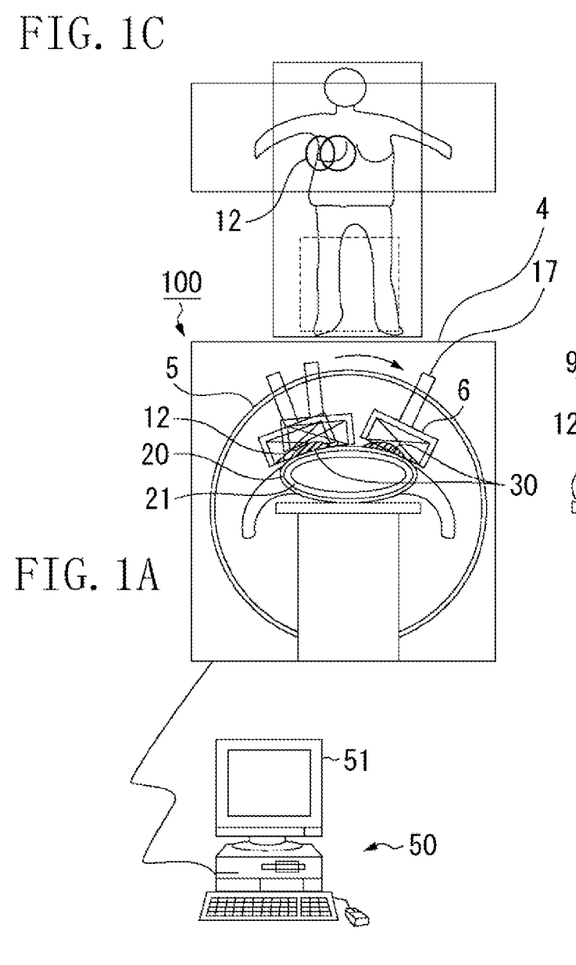
FIGS. 1A through 1C illustrate an entire configuration of a radiation imaging apparatus according to an exemplary embodiment of the invention.
Figure 1B:
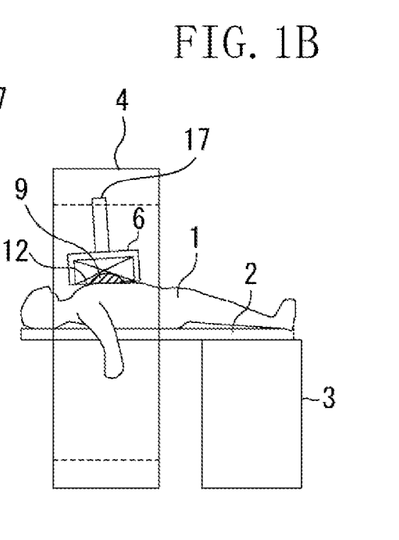

FIGS. 1A through 1C illustrate an entire configuration of a radiation imaging apparatus 100 according to an exemplary embodiment of the present invention. A subject 1 is laid on a table 2 in a supine position. A table support section 3 supporting the table 2 has a slide mechanism (not shown). By sliding the table 2, the subject 1 is inserted into a through hole section formed in a gantry 4. The gantry 4 is provided with a support frame 5 having a circular shape.

Referring to FIGS. 1A through 1C, the support frame 5 covers 360°. However, the support frame 5 may extend only in a shoulder direction of the subject 1 laid on the table 2 in a supine position. For example, the support frame 5 may be configured of only an upper circular portion.

The support frame 5 is provided with a scan frame 6 oriented to the subject 1. In the scan frame 6, a space portion or cavity is formed at the front-end portion thereof for receiving a breast as an examination object 9 of the subject 1.

The scan frame 6 is provided with an X-ray generation unit 7 and a two-dimensional X-ray detection unit 8 that are disposed opposite to each other being interposed by the space portion (refer to FIG. 2) such that they face one another. The scan frame 6 is adapted to rotate so that the X-ray generation unit 7 and the two-dimensional X-ray detection unit 8 are rotated around the breast as the examination object 9 while X-rays is emitted from the X-ray generation unit 7. Thus, X-ray transmission data of the examination object 9 is obtained (scanned) from multiple directions (360°).

A computer 50 is connected to the gantry 4 and functions as an operation console and an image-processing unit. The transmission data is subjected to an inverse Radon transform to reconstruct a cross section of the examination object 9 and the reconstructed image is displayed on a monitor 51.

Figure 2:
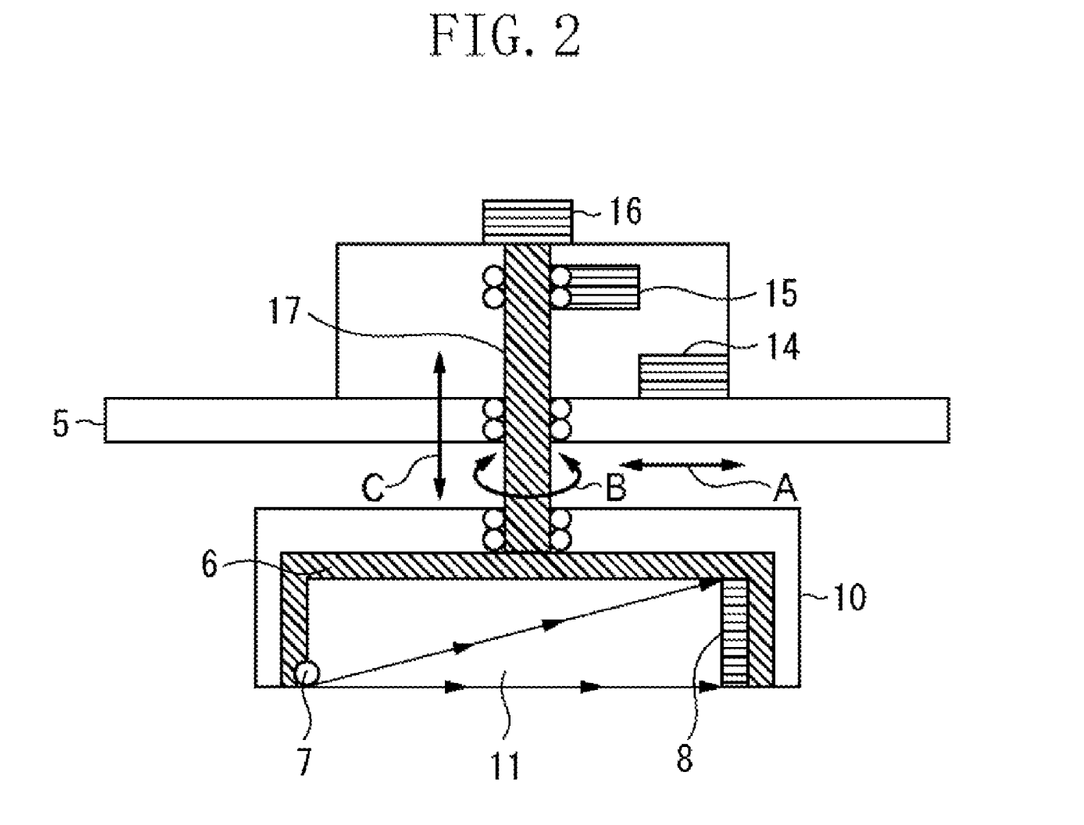
FIG. 2 illustrates a configuration of a scan frame according to the exemplary embodiment of the invention in detail.
Figure 3:
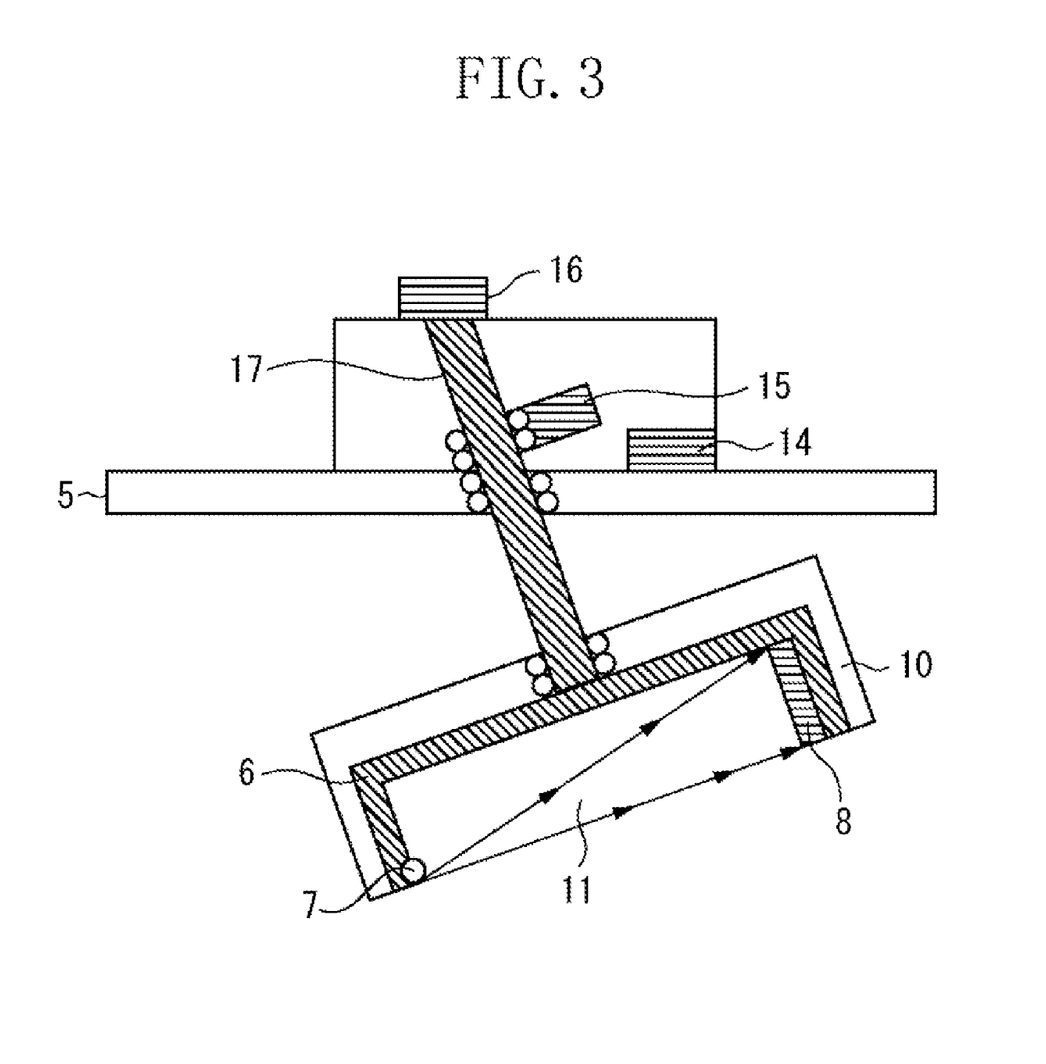
FIG. 3 illustrates a configuration of a scan frame according to the exemplary embodiment of the invention in detail.

FIG. 2 and FIG. 3 illustrate the scan frame 6 in detail. FIG. 2 illustrates the scan frame 6 that is vertically mounted on the support frame 5. The scan frame 6 is coated with a cover 10 to prevent the rotation portion from coming into direct contact with the subject 1. X-ray flux 11 emitted from the X-ray generation unit 7 is reformed by a collimator (not shown), and is projected only onto the two-dimensional X-ray detection unit 8.

Figure 4A:
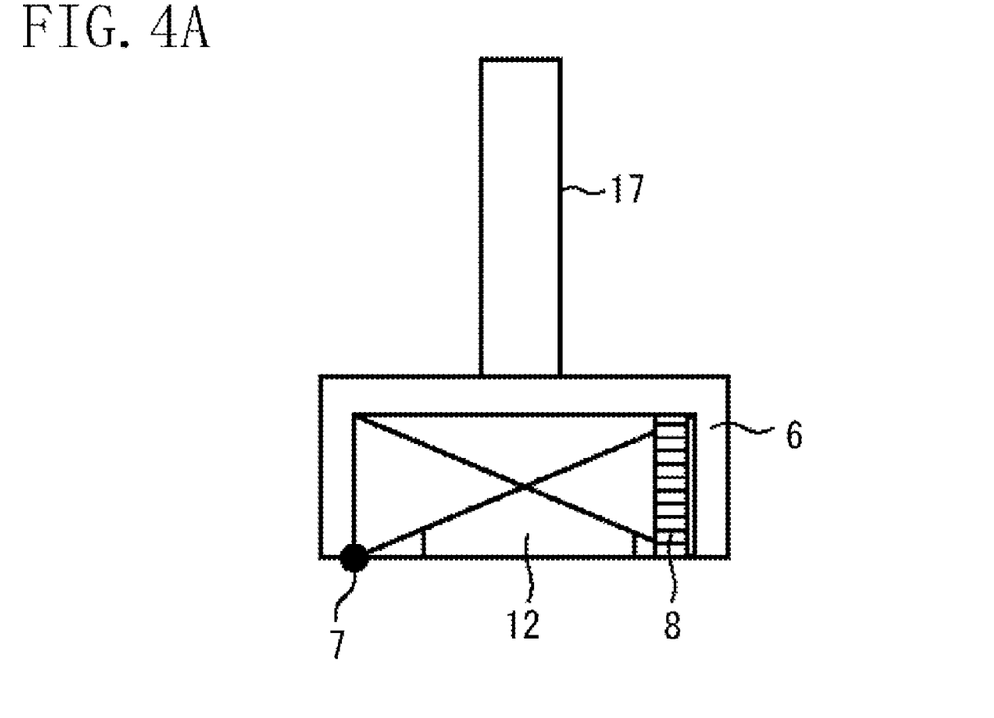
FIGS. 4A and 4B each illustrate a reconstruction area that is formed by the scan frame according to the exemplary embodiment of the invention.
Figure 4B:
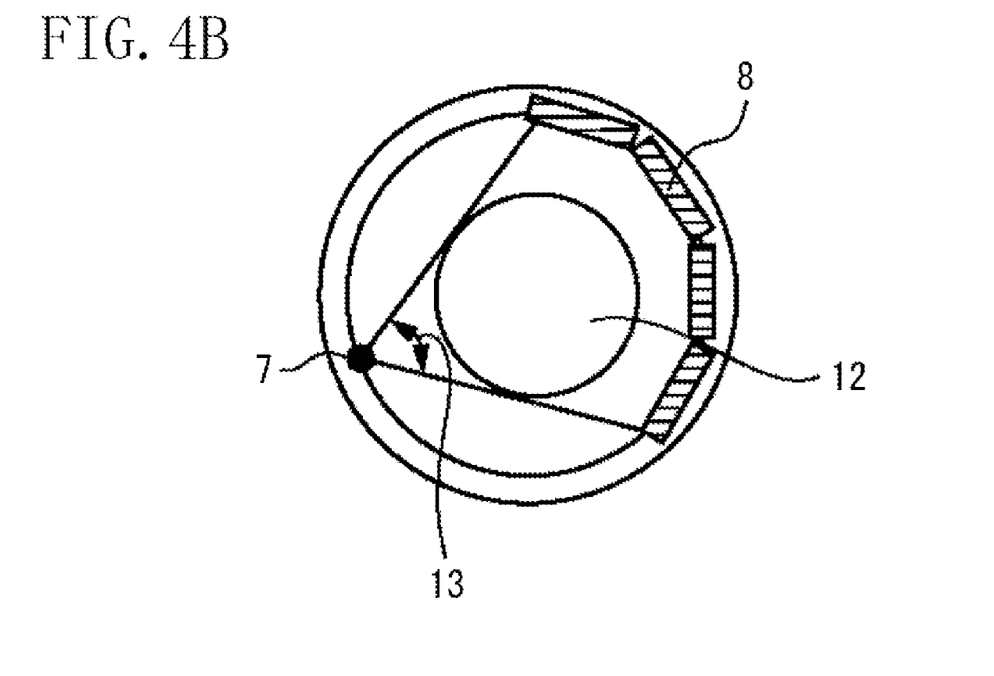

FIGS. 4A and 4B illustrate a reconstruction area 12 formed by the scan frame 6. As illustrated in FIGS. 4A and 4B, the reconstruction area 12 is determined depending on a fan angle 13. The scan frame 6 is slidably supported by the support frame 5, and a scan frame drive unit 14 changes the slide position of the scan frame 6 in the support frame 5 as illustrated in FIG. 2 (arrow-A). Additionally, the support frame 5 itself can rotate to shift the slide position of the scan frame 6.

The scan frame 6 is provided with a rotatable shaft or spin rod 17 extending thereabove as a rotation axle of the scan frame 6. The support frame 5 supports the spin rod 17. When a scan frame rotation drive unit 15 drives the shaft 17 to rotate, the scan frame 6 is driven to perform CT scan rotation (arrow-B) about the axis of the shaft.

The shaft 17 is provided with a conventional feed amount adjusting mechanism or a telescopic mechanism (not shown) to move the scan frame 6 along the axis of the shaft. The shaft 17 is provided with a scan frame angle/distance adjustment unit 16 that is mounted on the end portion thereof. The scan frame angle/distance adjustment unit 16 adjusts the slide position of the scan frame 6 in the support frame 5, the mounting angle of the scan frame 6 with respect to the support frame 5, and the feed amount (or retraction amount) of the shaft 17. As an alternative, the scan frame 6 may be adapted to rotate about a shaft 17 which does not itself rotate.

FIG. 3 illustrates the scan frame 6 the mounting angle of which is inclined with respect to the support frame 5. The scan frame angle/distance adjustment unit 16 adjusts the inclination angle of the spin rod 17 and the feed amount of the spin rod 17 (in a direction of arrow-C). With this arrangement, the distance between the scan frame 6 and the subject 1 can be adjusted.

The computer 50 performs reconstruction processing on the transmission data that is obtained by the two-dimensional X-ray detection unit 8 to convert the data into a multi-cross-section image; i.e., a three-dimensional image 18. The reconstruction processing is carried out with the inverse Radon transform.

The inverse Radon transform is carried out by, after filtering the transmission data, inversely projecting the same toward the focal point of the X-ray. The angle and position of the inverse projection is determined based on the slide position and angle of the scan frame 6 in the support frame 5, the feed length of the shaft 17, and the scan angle when the transmission data is obtained.

Figure 5:
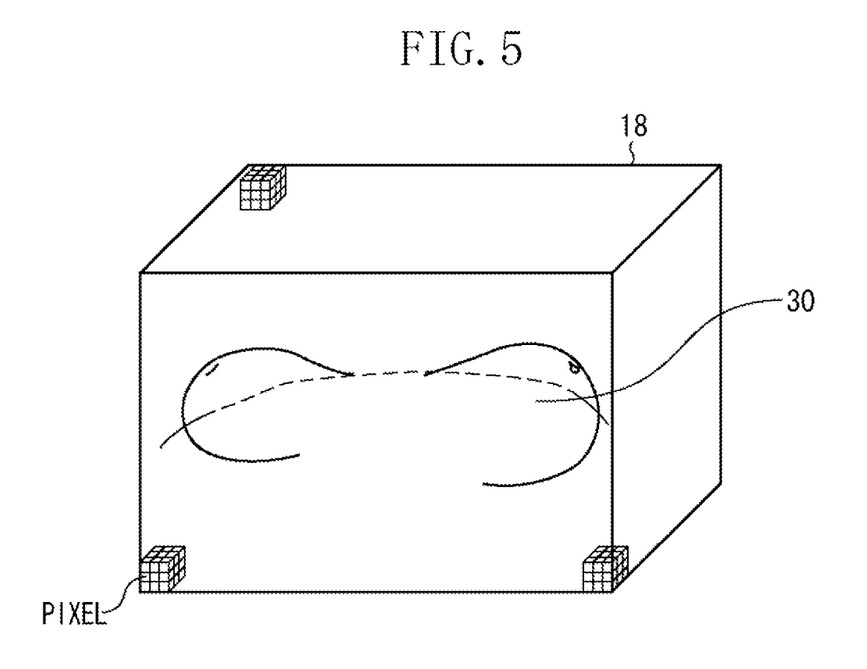
FIG. 5 illustrates a two-dimensional image of a reconstructed breast area.

As an example of the inverse Radon transform, the Feldkamp algorithm is given. As a reference to the inverse Radon transform, Feldkamp et al. "Practical ConeBeam Algorithm", J. Opt. Soc. Am. A1, 612-619, 1984 is available. FIG. 5 illustrates an example of a reconstructed three-dimensional image 18 of breasts 30.

Figure 16A:
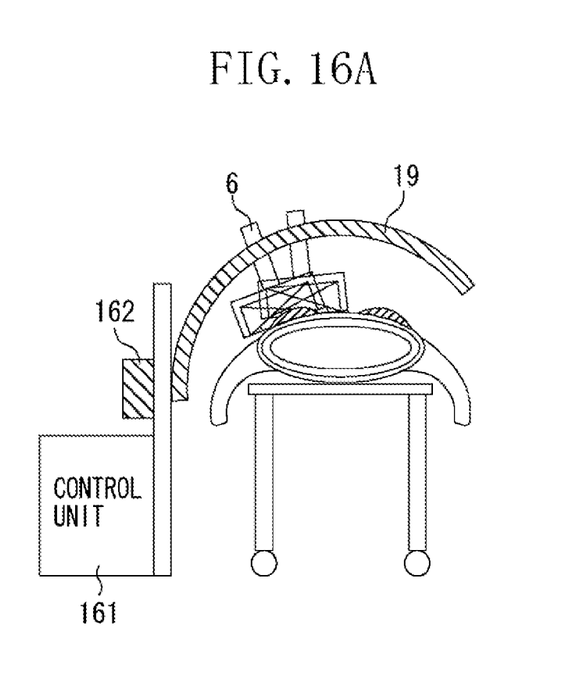
FIGS. 16A and 16B illustrate an entire configuration of a radiation imaging apparatus according to a modification of the invention.
Figure 16B:
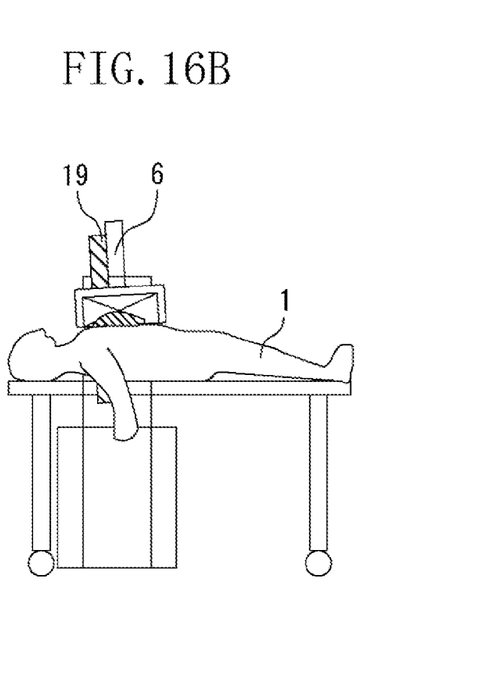

FIGS. 16A and 16B illustrate a modification of the radiation imaging apparatus 100 illustrated in FIGS. 1A through 1C. The support frame 5 is configured of a C-arm 19 and the C-arm 19 supports a scan frame 6. The scan frame 6 is capable of sliding on the C-arm 19 to change its position. Contrarily, the scan frame 6 may be fixed to the C-arm 19, and the position of the scan frame 6 may be changed when the feed amount of the C-arm is changed. Also, in place of adjusting the mounting angle of the C-arm 19 and the scan frame 6, a C-arm up/down rotating unit 162 may be driven to incline the C-arm 19 itself based on a control command from a control unit 161 to adjust the angle of the scan frame 6.

With the configuration as illustrated in FIGS. 1A through 1C or FIGS. 16A and 16B, breasts having different curvature shapes and sizes depending on the subject, can be flexibly handled and examined effectively. Further, the above-described configuration allows the subject to lie on the table in a supine position with arms pendent in a gravity direction. This configuration easily causes the curved outline formed by the chest around the breasts to be exposed. And this facilitates the examination in axillary portions that is indispensable for breast examination. Moreover, the above configuration enables the breast examination of the subject in a state lying in a supine position, and images of the breasts can be taken in a state similar to the posture during a surgical operation.

FIG. 1A is a front view of the radiation imaging apparatus 100, in which breasts and the vicinity thereof of the subject 1 are illustrated. The breast 30 belongs to a pectoral muscle 20 and the pectoral muscle 20 covers a rib 21. The radiation imaging apparatus 100 according to the exemplary embodiment covers breasts and the vicinity thereof including the pectoral muscle 20 as the examination object 9. When the scanning of the breasts is carried out including the rib 21, not only the subject 1 is exposed to an excessive radiation but also the obtained transmission data is inferior in signal value, which results in reconstructed images that are inferior in signal-to-noise ratio (S/N ratio). Therefore, according to the exemplary embodiment, the transmission data from the two-dimensional X-ray detection unit 8 is analyzed to adjust the angle of the scan frame 6 and the feed amount of the shaft 17.

Figure 6A:
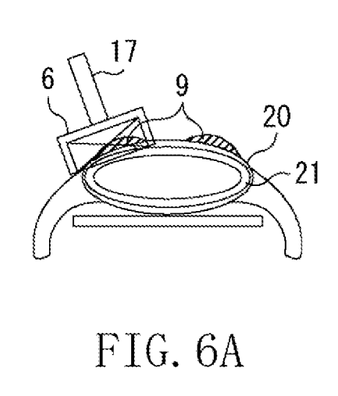
FIGS. 6A through 6C illustrate processing of transmission data obtained by the scan frame according to the exemplary embodiment of the invention.
Figure 6B:
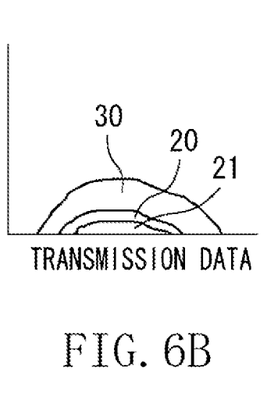
Figure 6C:
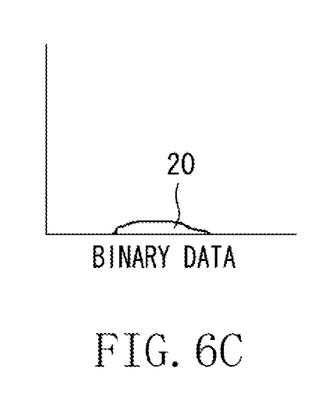

FIG. 6A is a sectional view illustrating a case in which the scan frame 6 is positioned too close to the breast 30 and the scanning is carried out including the rib 21. FIG. 6B illustrates the transmission data of the above. FIG. 6C illustrates binary data of the transmission data. When the X-ray passes through the rib 21 where the X-ray attenuates largely, the value of the transmission data decreases remarkably. Therefore, when the transmission data is subjected to a binary process using a predetermined threshold, it is possible to determine whether the scanning is carried out including the rib 21 and obtain the area of rib 21.

Figure 7A:
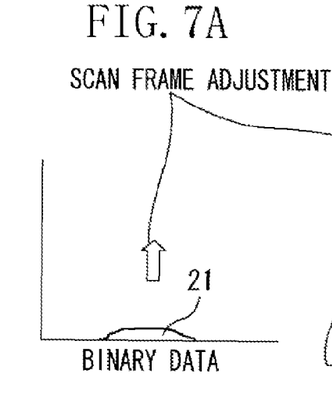
FIGS. 7A through 7C illustrate positional adjustment of the scan frame based on the transmission data according to the exemplary embodiment of the invention.
Figure 7B:
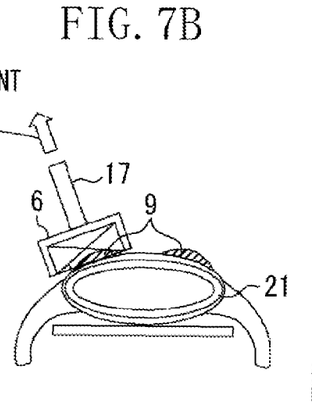
Figure 7C:
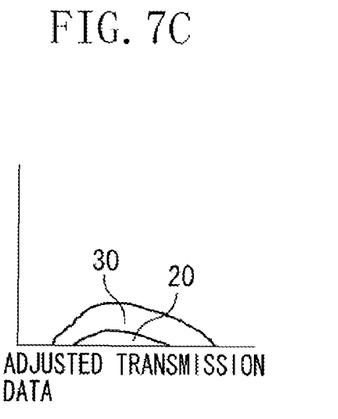

FIGS. 7A through 7C illustrate an example of an adjustment result of the angle of the scan frame 6 and the feed amount of the shaft 17 based on the binary data of FIG. 6. The analysis of the transmission data and the adjustment of the angle of the scan frame 6 and the feed amount of the shaft 17 are carried out in real time while the scan frame 6 performs rotational scanning. By simultaneously performing the adjustment of the feed amount and rotational scanning with the scan frame 6, the time required for taking X-ray images can be reduced.

Figure 8A:
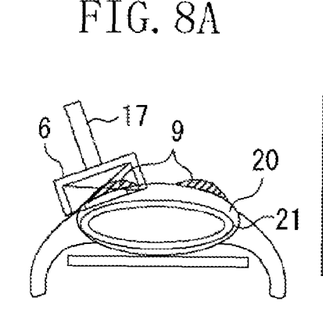
FIGS. 8A through 8C illustrate positional adjustment of the scan frame using a histogram analysis according to the exemplary embodiment of the invention.
Figure 8B:
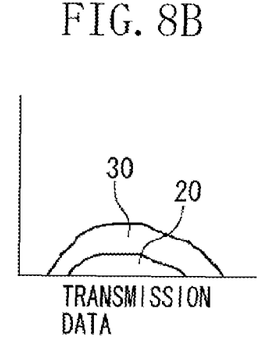
Figure 8C:
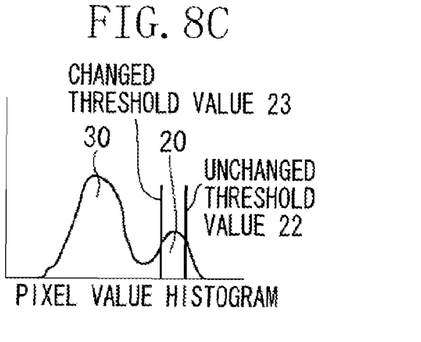

Referring to FIGS. 6A through 6C and FIGS. 7A through 7C, the scan frame 6 is controlled so that the rib 21 is not included in the transmission data. There may be a case that the subject 1 has a thick pectoral muscle 20. The pectoral muscle 20 largely attenuates the X-ray. In such a case, the scan frame 6 has to be controlled to thinly scan the pectoral muscle 20. For that purpose, based on a histogram analysis, the predetermined threshold 22 for binarization processing may be changed to a threshold 23 as illustrated in FIGS. 8A through 8C.

To take a CT scan image of the breast in cross section, the scan frame 6 has to be positioned as close to a chest wall as possible. To position the scan frame 6 as close to the chest wall as possible, if a contact detection device or the like is used, it may impose a considerable burden on the subject 1. However, if the angle of the scan frame 6 and the feed amount of the spin rod 17 are adjusted based on the above-described transmission data, it is advantageous because no contact detection device is used.

Now, a description is given about the method of planning the adjustment of the mounting angle and slide position of the scan frame 6 in the support frame 5 and the feed amount of the shaft 17 based on CT data of the entire body. The CT data of the entire body is a tomogram of the entire chest of a subject, including the breasts.

Figure 9A:
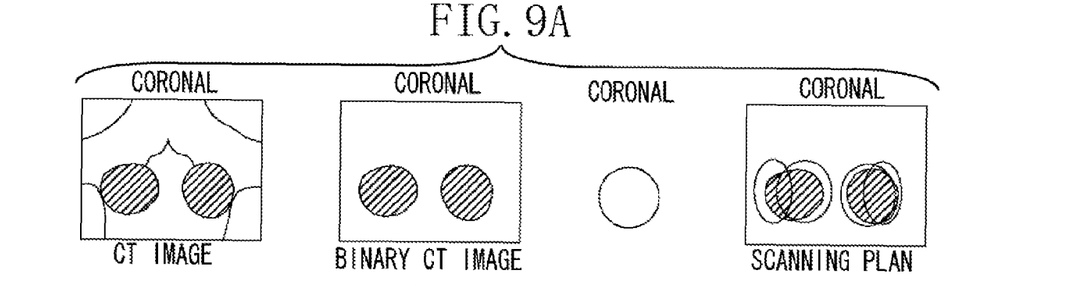
FIGS. 9 and 9B illustrate scan planning based on CT data of the entire body according to the exemplary embodiment of the invention.
Figure 9B:
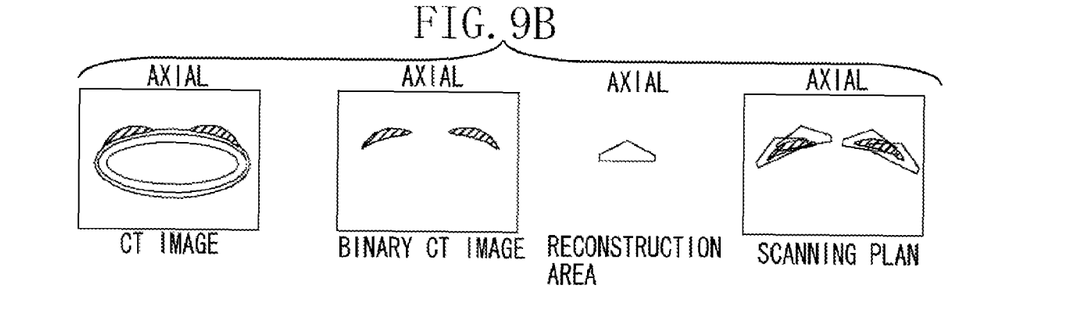

FIGS. 9A and 9B illustrate examples of a tomogram of the entire chest including the breasts 30. The tomogram is taken with an entire body CT scan apparatus or an entire body MRI apparatus that is capable of taking tomograms of the entire chest including breasts of a subject. By subjecting the tomogram obtained from the entire body CT to a binarization processing using a predetermined threshold, the three-dimensional volume of the breast area can be determined.

An area that can be covered by one scan is also determined three-dimensionally as illustrated in FIGS. 4A and 4B. Therefore, when the breasts 30 are too large, the scanning is planned so as to be carried out a plurality of times on each of the breasts 30. An operator carries out the positional planning of the scan frame 6 in the following manner. That is, a binary-processed image (examination object 9) is displayed on the monitor 51 of the computer 50 and the reconstruction area 12 is superimposed thereon.

The computer 50 may automatically carry out the above processing. When the computer 50 carries out the processing automatically, the computer 50 obtains the volume of the right and left breasts 30. And then, the computer 50 determines whether each of the volume, height and plane area of the respective breasts 30 can be covered in the reconstruction area 12 by one scan.

Figure 13:
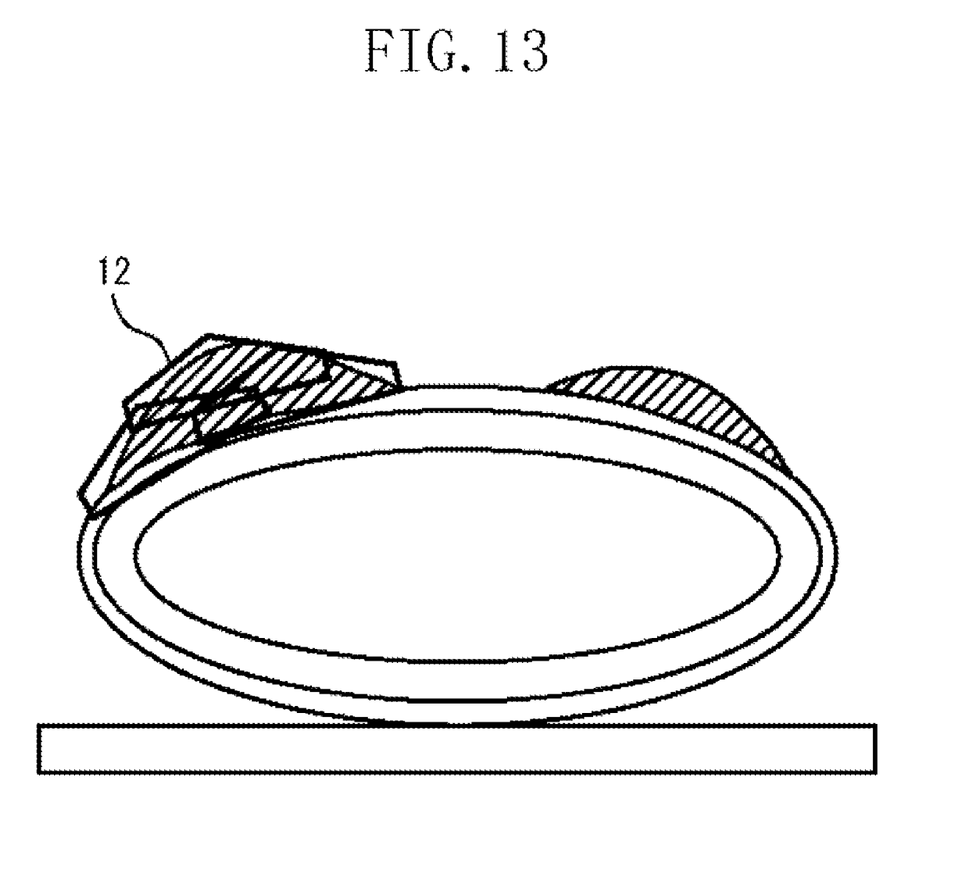
FIG. 13 illustrates an example in which an examination object is divided and the scan is carried out several times.

When any of the volume, height and plane area of the respective breasts 30 cannot be covered by one scan, the computer 50 calculates how many times the reconstruction area corresponding to one scan the volume of the breast corresponds to. If the number of scans is thus determined, the volume of the breast is divided by the number of the scan times and the scan is planned so that the scan center coincides with the gravity center of the divided areas (refer to FIG. 13).

A scanning operator carries out adjustment of the reference point for the scan plan that is made based on the CT data of the entire body and the scan frame 6 that performs CT scanning with the radiation imaging apparatus 100, by disposing the scan frame 6 at the predetermined first scan position. Here, as for the CT data of the entire body, only an outline of the chest is required for scan planning. Therefore, the scanning is carried out with low levels of radiation.

Figure 10:
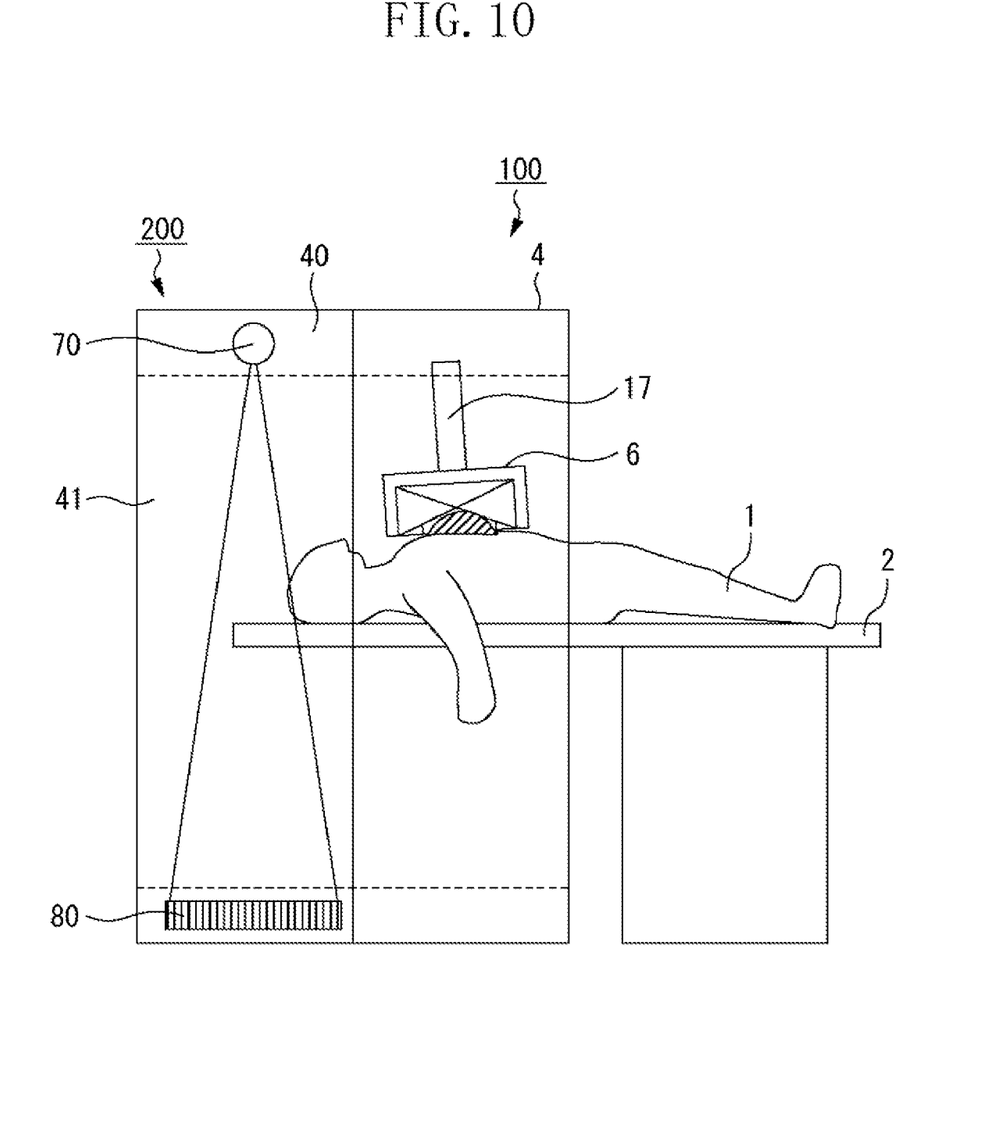
FIG. 10 illustrates an example of a configuration of a radiation imaging apparatus further including an entire body CT scan apparatus.

FIG. 10 illustrates an example of a configuration of a radiation imaging apparatus that further includes an entire body CT scanner apparatus 200. The entire body CT scanner apparatus 200 is provided with a gantry 40 having a hollow portion 41 for inserting the subject 1 laid on a table 2.

The gantry 40 is provided with an X-ray generation unit 70 and an X-ray detection unit 80 at a position opposite to the X-ray generation unit 70 being interposed by the hollow portion 41. The X-ray generation unit 70 and the X-ray detection unit 80 are rotated around the hollow portion 41 to scan the entire body.

An advantage of this configuration is the positional relationship between the CT data obtained by the radiation imaging apparatus 100 and the CT data of the entire body obtained by the entire body CT scanner apparatus 200 is known. Therefore, reference point adjustment between the scan plan based on the CT data of an entire body, and the scan frame 6 for CT scanning with the radiation imaging apparatus 100 is not required.

Now, the planning of adjustment of the slide position and the mounting angle of the scan frame 6 in the support frame 5 and the feed amount of the shaft 17 based on a two-dimensional or a three-dimensional fluoroscopic image that is obtained by prescanning using the two-dimensional X-ray detection unit 8 is described.

Figure 11A:
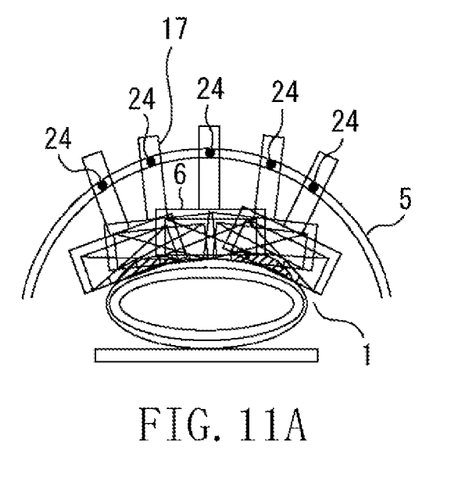
FIGS. 11A and 11B illustrate an example of milestone setting and a generated image based on the scan plan according to the exemplary embodiment of the invention.
Figure 11B:
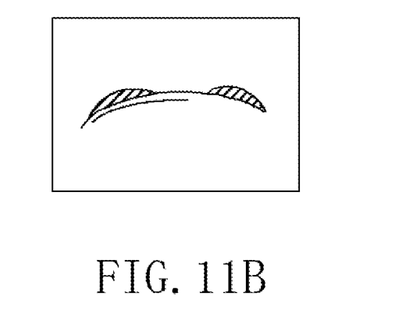

FIGS. 11A and 11B illustrate a method of prescanning. The subject 1 is laid on the table 2 in a supine position as illustrated in FIG. 11A. An operator registers a plurality of reference positions 24 along the curved outline of the chest of the subject 1 using a switch or the like (not shown).

The computer 50 computes a curved line that passes through the registered reference positions 24 and controls the scan frame 6 so as to continuously move while emitting low level X-rays. While moving the scan frame 6, the computer 50 adjusts the position and the angle of the scan frame 6 in the support frame 5 and the feed amount of the shaft 17.

There are two methods for performing the prescanning. That is, prescanning while rotating the scan frame 6 and prescanning without rotating the scan frame 6.

When the scan frame 6 is not rotated, the slide position of the scan frame 6 in the support frame 5 is fixed and transmission data is obtained at a plurality of slide positions in the support frame 5 (for example, at the positions of the respective reference positions 24). Such shifting of the scan frame 6 is referred to as "stepping movement". With the prescanning performed in the above stepping movement, a two-dimensional fluoroscopic image is obtained as illustrated in FIG. 11B.

On the other hand, when the scan frame 6 is rotated, the prescanning is carried out in the following manner. That is, while rotating the scan frame 6, the scan frame 6 is continuously moved along the support frame 5 in synchronization with the rotation to obtain transmission data. In this case, each of the X-ray generation unit 7 and the two-dimensional X-ray detection unit 8 makes a spiral movement. Therefore, the movement is referred to as "spiral movement" and the obtained transmission data is referred to as "spiral data".

Figure 12A:
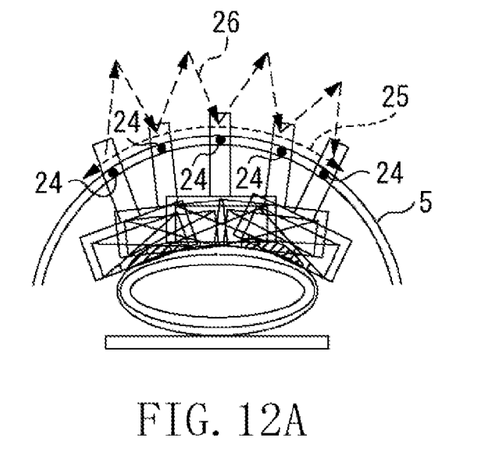
FIGS. 12A and 12B illustrate prescanning carried out with stepping movement and spiral movement.

FIG. 12A illustrates the prescanning in a stepping movement and a spiral movement. A broken line 25 represents an example locus of the spiral movement, and a broken line 26 represents an example locus of the stepping movement. With any of the movement methods, when the scan frame 6 is rotated, a three-dimensional image 18 of the breast 30 on the chest wall as illustrated in FIG. 5 is obtained. The purpose of the prescanning is planning of the main scan and determining of the outline of the examination object 9. Therefore, the prescanning may be carried out using a lower radiation dose level than that for the main scan.

Figure 12B:
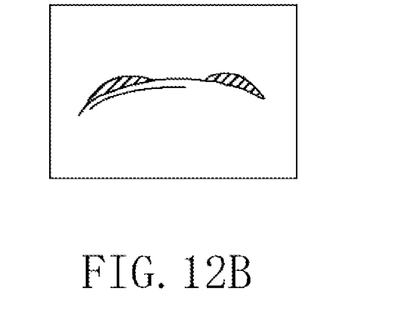

When the scan frame 6 is not rotated, the direction of the X-ray generation unit 7 and the two-dimensional X-ray detection unit 8 is adapted so that the imaging of the breast area is carried out in a longitudinal direction of the body of the subject 1 (in a movement direction of the table 2). FIG. 12B illustrates an example of a two-dimensional fluoroscopic image that is generated by the prescanning with the stepping movement without rotating the scan frame 6.

Based on the transmission data obtained by the above-described prescanning, the adjustment of the position and the angle of the scan frame 6 in the support frame 5 and the feed amount of the shaft 17 can be planned. The planning of the adjustment may be determined by the operator or may be automatically carried out by the computer 50 as described above.

Image reconstruction processing of the transmission data taken in the manner of spiral movement is also carried out with the inverse Radon transform. The angle and the position of inverse projection in the inverse Radon transform are determined based on the position and the angle of the scan frame 6 in the support frame 5, the feed amount of the shaft 17 and the scan angle when the transmission data is obtained.

It can be also selected in a main scan whether the scan is carried out in a first main scan of the stepping movement or in a second main scan of the spiral movement. The second main scan of the spiral movement has an advantage that there is no vertical movement of the scan frame 6, and thus the scan time is shorter than that of the first main scan of the stepping movement.

The selection of whether to carry out the first main scan of the stepping movement or to carry out the second main scan of the spiral movement may be made by the operator, or may be automatically made based on the size of the breast 30 by processing the image.

For example, it is determined whether the reconstruction area 12 by a single scan can cover the volume, height and plane area of the breast 30. When it is determined based on the volume, height and plane area of the breast 30 that if the spiral movement is carried out, the breast 30 may come into contact with the cover 10 of the scan frame 6 and the breast 30 may be deformed, the first main scan of the stepping movement is selected. To be more particular, when the height of the breast exceeds the height of the reconstruction area 12 or when the plane area of the breast exceeds the scan diameter of the scan frame 6, the first main scan of the stepping movement is selected.

When the examination object 9 is smaller than the reconstruction area 12 or when the scan is carried out a plurality of times and the divided examination object 9 is smaller than the reconstruction area 12, the subject is exposed to excessive radiation. Such excessive radiation should be reduced as much as possible.

Figure 14A:
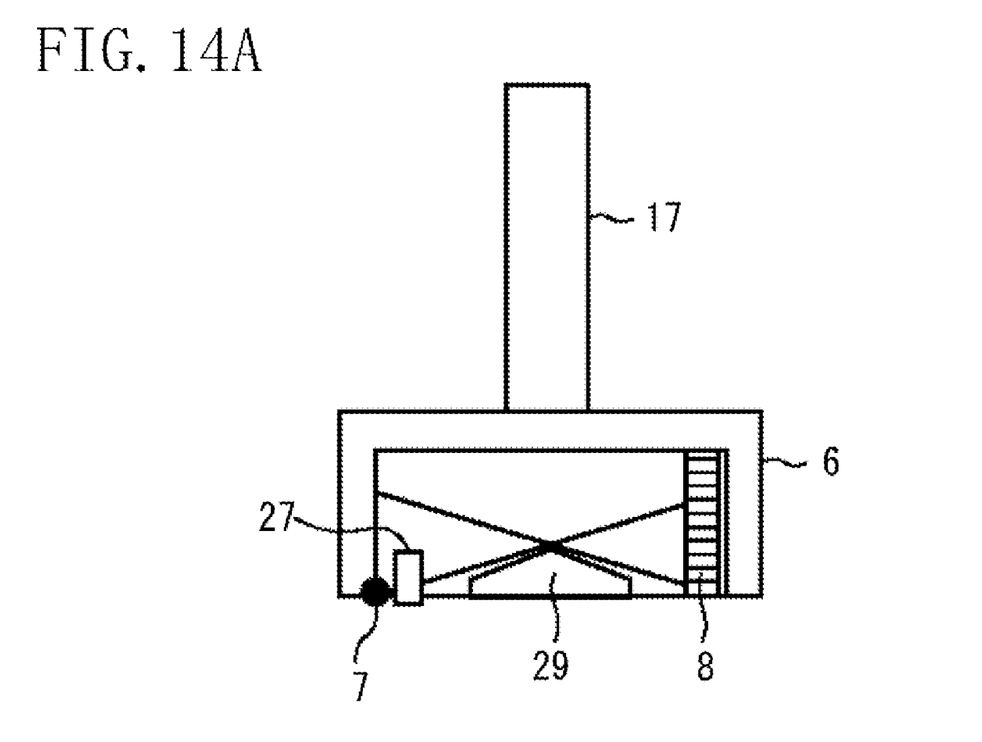
FIGS. 14A and 14B illustrate an example in which an X-ray flux modification section is provided for reducing the reconstruction area.
Figure 14B:
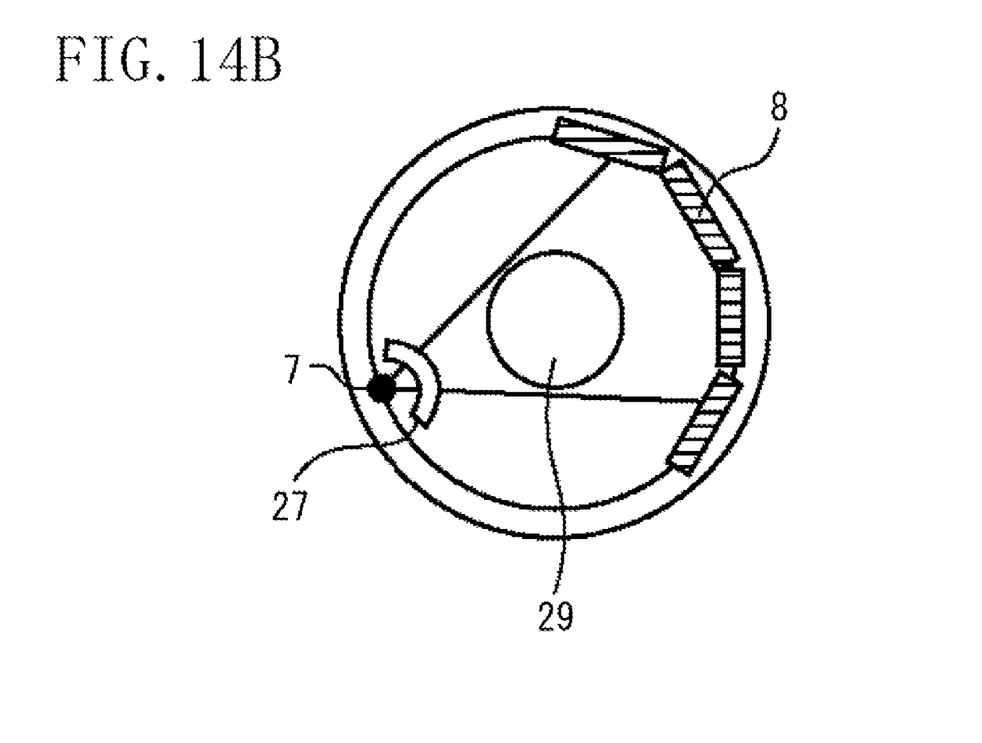

Therefore, an X-ray flux modification section 27 may be provided in front of the X-ray generation unit 7 as illustrated in FIGS. 14A and 14B to modify the radiation range of the X-rays emitted from the X-ray generation unit 7. With this arrangement, the X-ray flux is modified and the reconstruction area 29 in which the reconstruction area 12 is reduced can be formed.

Figure 15:
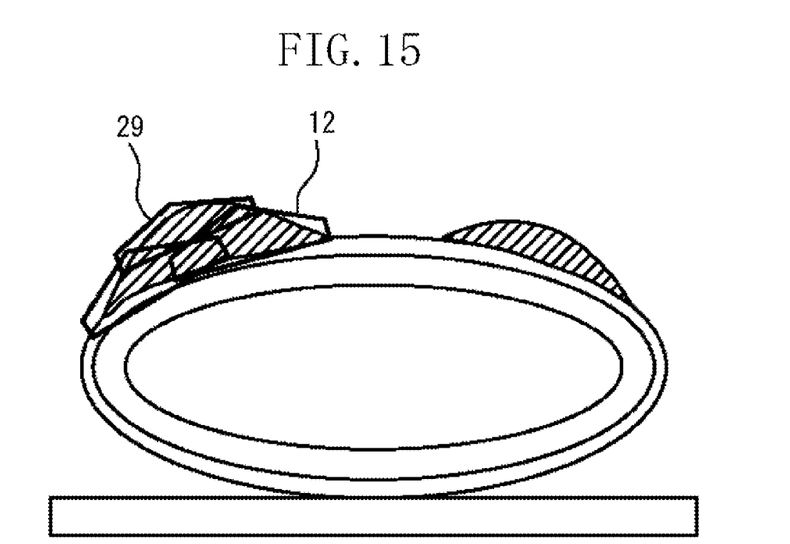
FIG. 15 schematically illustrates a scan in which a standard reconstruction area is divided into smaller reconstruction areas and the scanning is repeated three times.

For example, when it is determined during the scan planning that such excessive exposure area is generated, an instruction can be given to the X-ray flux modification section 27 to reduce the X-ray radiation range emitted from the X-ray generation unit 7. FIG. 15 schematically illustrates scanning in which a standard reconstruction area 12 is divided into smaller reconstruction areas 29 and the scanning is carried out three times.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2007-189992 filed Jul. 20, 2007, which is hereby incorporated by reference herein in its entirety.

What is claimed is:

1. A radiation imaging apparatus adapted to perform radiation imaging of a breast of a subject, comprising:
   a table for supporting a subject in a supine position;
   a receiving section configured to receive a breast of the subject whilst in said supine position;
   a radiation imaging section including a radiation emission unit and a radiation detection unit which face each other and which have the breast of the subject interposed therebetween when the breast is received in the receiving section; and
   a drive unit operable to move the receiving section to a position suitable for imaging the breast of the subject.

2. The radiation imaging apparatus according to claim 1, wherein the drive unit includes:
   a shaft having an axis about which the receiving section is rotatable, the shaft being capable of adjusting the relative position of the receiving means with respect to a breast of the subject along said axis of the shaft;
   a support frame that extends in a plane substantially perpendicular to the longitudinal axis of the subject in said supine position, the support frame being arranged to slidably support the receiving section via the shaft; and
   an adjustment section configured to adjust at least one of: a slide position of the receiving section in the support frame; a mounting angle of the receiving section with respect to the support frame; and a relative position of the receiving means with respect to the subject along said axis of the shaft.

3. The radiation imaging apparatus according to claim 2, comprising means for obtaining images by carrying out prescanning at a plurality of slide positions while shifting the receiving section in the support frame without rotating the receiving section on the axis of the shaft,
   the adjustment section being configured to adjust at least one of: the slide position of the receiving section in the support frame; the mounting angle of the receiving section in the support frame; and the relative position of the receiving means with respect to the subject along said axis of the shaft, based on the obtained images.

4. The radiation imaging apparatus according to claim 2, comprising means for obtaining images by carrying out prescanning at a plurality of slide positions while shifting the receiving section in the support frame and rotating the receiving section on the axis of the shaft,
   the adjustment section being configured to adjust at least one of: the slide position of the receiving section in the support frame; the mounting angle of the receiving section in the support frame; and the relative position of the receiving means with respect to the subject along said axis of the shaft, based on the obtained images.

5. The radiation imaging apparatus according to claim 1, wherein the drive unit is operable to move the receiving section based on transmission data from the radiation imaging section.

6. The radiation imaging apparatus according to claim 1, including a control unit configured to determine whether the radiation entering into the radiation detection unit has passed through a high attenuation area of the subject, wherein the drive unit moves the receiving section based on the result of such a determination.

7. The radiation imaging apparatus according to claim 1, further comprising an entire body imaging apparatus capable of providing a tomogram of an entire chest including a breast of the subject,
wherein the drive unit is operable to move the receiving section based on a tomogram of the entire chest including the breast of the subject provided by the entire body imaging apparatus.

8. The radiation imaging apparatus according to claim 1, further comprising a selection unit configured to select whether to carry out either a first main scan at a plurality of slide positions while shifting the receiving section in the support frame without rotating the receiving section about the axis of the shaft, or a second main scan at a plurality of slide positions while rotating the receiving section about the axis of the shaft and shifting the receiving section in the support frame.

9. The radiation imaging apparatus according to claim 8, wherein the selection unit is configured to perform the selection based on images obtained by pre-scanning or based on a tomogram of an entire chest including a breast of the subject.

10. The radiation imaging apparatus according to claim 1, wherein the receiving section further includes a radiation flux modification section that modifies a radiation range of the radiation emitted from the radiation emission unit.

* * * * *